US012070578B2

(12) United States Patent
Meng et al.

(10) Patent No.: US 12,070,578 B2
(45) Date of Patent: Aug. 27, 2024

(54) MEDICAL TUBING DIMENSION SCANNING

(71) Applicant: CareFusion 303, Inc., San Diego, CA (US)

(72) Inventors: Fanqing Meng, Buffalo Grove, IL (US); Marc Weimer, South Jordan, UT (US); Daniel Kimm, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 1023 days.

(21) Appl. No.: 16/823,405

(22) Filed: Mar. 19, 2020

(65) Prior Publication Data

US 2020/0330683 A1 Oct. 22, 2020

Related U.S. Application Data

(60) Provisional application No. 62/836,353, filed on Apr. 19, 2019.

(51) Int. Cl.
*A61M 5/168* (2006.01)
*A61M 5/142* (2006.01)

(52) U.S. Cl.
CPC ........ *A61M 5/16831* (2013.01); *A61M 5/142* (2013.01); *A61M 2005/16863* (2013.01); *A61M 2205/18* (2013.01); *A61M 2205/3306* (2013.01); *A61M 2205/3327* (2013.01); *A61M 2205/3331* (2013.01); *A61M 2205/3334* (2013.01);
(Continued)

(58) Field of Classification Search
CPC .... A61M 5/16831; A61M 2005/16863; A61M 5/14; A61M 5/16854; A61M 5/16859; A61M 5/16877; A61M 5/142; A61M 2005/14208; A61M 5/14212; A61M 5/14228; A61M 5/14216; A61M 5/14222; A61M 2205/18; A61M 2205/3306; A61M 2205/3327; A61M 2205/3331;
(Continued)

(56) References Cited

U.S. PATENT DOCUMENTS 5,096,385 A 3/1992 Georgi et al.
5,116,203 A 5/1992 Natwick et al.
(Continued)

FOREIGN PATENT DOCUMENTS

CN 1494651 A 5/2004
CN 102196832 A 9/2011
(Continued)

OTHER PUBLICATIONS

International Search Report and Written Opinion for Application No. PCT/US2020/028365, dated Jul. 1, 2020, 17 pages.
(Continued)

*Primary Examiner* — Jason E Flick
(74) *Attorney, Agent, or Firm* — Morgan, Lewis & Bockius LLP

(57) ABSTRACT

Pump assemblies for fluid flow are provided. A pump assembly includes a fluid flow pump, a first tubing pathway configured to receive a fluid input tube and a second tubing pathway configured to receive a fluid output tube. A non-contact tubing dimension measurement assembly is configured to measure a tubing outside diameter (OD). Methods of operating a fluid flow pump are also provided.

19 Claims, 7 Drawing Sheets

(52) U.S. Cl.
CPC .............. *A61M 2205/3375* (2013.01); *A61M 2205/3576* (2013.01); *A61M 2205/50* (2013.01)

(58) Field of Classification Search
CPC .. A61M 2205/3334; A61M 2205/3375; A61M 2205/50; A61M 2205/33; A61M 2205/332
See application file for complete search history.

(56) References Cited

U.S. PATENT DOCUMENTS

| | | | |
|---|---|---|---|
| 5,720,721 A * | 2/1998 | Dumas | A61M 5/16854 604/118 |
| 5,853,386 A * | 12/1998 | Davis | A61M 5/16854 128/DIG. 13 |
| 5,935,106 A | 8/1999 | Olsen | |
| 6,358,225 B1 | 3/2002 | Butterfield | |
| 7,578,165 B1 * | 8/2009 | Stupecky | G01B 11/08 356/627 |
| 2010/0106082 A1 * | 4/2010 | Zhou | A61M 5/14232 604/67 |
| 2012/0179131 A1 * | 7/2012 | Butterfield | A61M 5/14212 604/67 |
| 2014/0350513 A1 | 11/2014 | Oruklu et al. | |

FOREIGN PATENT DOCUMENTS

| | | |
|---|---|---|
| CN | 103328020 A | 9/2013 |
| WO | WO-8400691 | 3/1984 |
| WO | WO-9804301 | 2/1998 |
| WO | WO-2013176770 | 11/2013 |
| WO | WO-2016044146 | 3/2016 |
| WO | WO-2016209554 A1 | 12/2016 |

OTHER PUBLICATIONS

Chinese Office Action for Application No. 202080043993.4, dated Feb. 23, 2024, 21 pages including translation.

* cited by examiner

Table 1: Tubing OD change vs variable vacuum pressure

|  | Test 1 | | Test 2 | | Test 3 | |
| --- | --- | --- | --- | --- | --- | --- |
|  | Vacuum (psi) | OD (Inch) | Vacuum (psi) | OD (Inch) | Vacuum (psi) | OD (Inch) |
|  | 0 | 0.1275 | 0 | 0.1255 | 0 | 0.1252 |
|  | 3.4 | 0.1254 | 2.8 | 0.1232 | 2.8 | 0.1238 |
|  | 5.6 | 0.1229 | 5.9 | 0.1189 | 4.8 | 0.1216 |
|  | 8.9 | 0.1178 | 9.1 | 0.1119 | 8.9 | 0.1156 |
|  | 12.2 | 0.1075 | 12 | 0.1045 | 12.1 | 0.1086 |
|  | 13.4 | 0.103 | 13.3 | 0.099 | 13.2 | 0.1031 |
| OD change from initial to end (%) |  | 19.2 |  | 21.1 |  | 17.7 |

MEDICAL TUBING DIMENSION SCANNING

CROSS-REFERENCES TO RELATED APPLICATIONS

This Application claims the benefit of U.S. Provisional Patent Application No. 62/836,353 entitled "MEDICAL TUBING DIMENSION SCANNING," filed on Apr. 19, 2019, the disclosure of which is hereby incorporated by reference in its entirety for all purposes.

TECHNICAL FIELD

The present disclosure generally relates to infusion pump occlusion detection, in particular non-contact tubing dimension measurement and a feedback loop.

BACKGROUND

Flexible tubing for medical fluid transfusion has been widely used in the medical field for intravenous (IV), epidural, and enteral applications. A prevailing upstream occlusion detection method, for instance, used in a typical infusion pump, is an upstream force sensor. The force sensor precedes the pumping mechanism and measures the force of the pumping tubing segment when constrained within the gap between the platen and force gauge. Alternatively, an optional back-support part holds the tubing in place where the tubing physically contacts the force gauge under the compression in the pump. The pump software and/or algorithms determines if an occlusion exists by looking at the pressure change over a given time period.

The tubing becomes stressed (e.g., compressed) when the tubing is loaded in place and the pump door is closed. The stress induced tubing stress relaxation or "creep" that results from a softer tubing. False upstream occlusion alarms are often experienced by observing stress relaxation of the tubing material upon loading the tubing into the pump. In this case, forces observed by the upstream pressure sensor can drop at a rapid rate and can be mistaken as false occlusion alarm.

Multiple sources of variation occurs in the tubing force measurement. There are pump-to-pump variations in gap size, which alters the compressive force on the tubing. Other sources of variation include tubing compliance variation from resin formulation, sterilization, age, creep, set handling by healthcare practitioner or manufacturing variances in geometry, assembled length or other factors. There are also fluid pressure fluctuations, as may be imparted by the pumping mechanism that introduce noise to the pressure measurement and can result in false occlusion alarms. Yet another source of force measurement variation are component variance and drift. In addition, there are environmental factors such as temperature changes and atmospheric pressure effects.

Further, during fluid delivery cycles, an upstream occluder valve is opened and a downstream valve is closed for the fluid filling, then the upstream valve is closed and the downstream valve opened, following up with a pump plunger physical touching the tubing to squeeze out the medical fluid. After that, the plunger lifts up to wait for the compressed tubing to recover for the next refilling cycle. However, the tubing typically cannot recover itself to the original round shape under some circumstances that include factors of tubing stress relaxation, loss of elasticity under low temperature, and slow rebound speed under high flow rate, to name a few. Therefore, the measured delivery volume is under the targeted volume range. Thus, knowing accurately the filled fluid volume of each cycles is very critical for a controlled delivery to patients.

In order to accommodate the variations from the manufacture of pumps and tubing, as well as accommodate environmental factors that introduce measurement variation to existing force gauge technology, it is desirable to provide a non-contact tubing dimension measurement system to improve occlusion alarm sensitivity and consistency, as well as reduce the occurrence of false alarms upstream.

It is also desirable to provide a feedback loop mechanism to communicate the measurement of tubing deformation dynamics to adjust pumping rate during delivery to improved flow delivery accuracy. Accordingly, a non-contact method is provided to measure the tubing OD change of each pumping cycle in real time and provide feedback to the pump with a pre-determined transfer function of OD and filled volume.

SUMMARY

One or more embodiments of the disclosure provide for a pump assembly. The pump assembly includes a fluid flow pump, a tubing pathway configured to receive a fluid tube and a tubing dimension measurement assembly. The tubing dimension measurement assembly includes a processor, an emitter spaced from the tubing pathway and configured to generate an emission into the tubing pathway, and a collector spaced from the tubing pathway, the collector disposed to receive the emission from the emitter, wherein the tubing dimension measurement assembly is further configured to measure an outside diameter (OD) of a tube received in the pathway, wherein said measurement is based at least in part on the emission.

In one or more aspects, the fluid flow pump is an infusion pump. In one or more aspects, the tubing dimension measurement assembly is disposed on a portion of the tubing pathway receiving a fluid input tube. In one or more aspects, the tubing dimension measurement assembly is disposed either internal or external to the fluid flow pump. In one or more aspects, the tubing dimension measurement assembly comprises a laser scanning system including the emitter and the collector. In one or more aspects, the laser scanning system includes one of a single-axis, dual-axis, a triple-axis and a quartic-axis scanning laser micrometer. In one or more aspects, the tubing dimension measurement assembly comprises an ultrasonic scanning system including the emitter and the collector. In one or more aspects, the tubing dimension measurement assembly is further configured to monitor a change in measurements of the OD in real time during operation of the fluid flow pump.

In one or more aspects, the processor is configured to detect a change in the OD exceeding an occlusion dimension change threshold. In one or more aspects, the processor is further configured to cause presentation of an alarm upon detecting that the established occlusion dimension change threshold is exceeded. In one or more aspects, the tubing dimension measurement assembly is configured to detect a tubing refilled position of each pumping cycle. In one or more aspects, the processor is configured to measure a change in the tubing OD with a predetermined measured OD vs. volume equation or table. In one or more aspects, the processor is configured to generate a signal based on the measured change in OD, wherein the signal causes an adjustment to at least one operational characteristic of the pump assembly. In one or more aspects, the pump assembly includes an output device, and wherein the adjustment includes activating the output device based on the signal to provide a perceivable indication of the change in OD. In one or more aspects, the fluid flow pump is configured to adjust a pumping rate based on receipt of the signal to maintain a predetermined flow rate accuracy range.

One or more embodiments of the disclosure provide for a method of operating a fluid flow pump. The method includes disposing tubing in a fluid flow pathway of a fluid flow pump. The method also includes causing the fluid flow pump to perform one or more pumping cycles, wherein each pumping cycle forces fluid flow from an output end of the tubing by exerting at least one force on a first portion of the tubing. The method includes measuring, by a non-contact tubing dimension measurement assembly, a tubing outside diameter (OD) of the first portion of the tubing.

In one or more aspects, the method includes determining a change in the tubing OD in real time during operation of the fluid flow pump. In one or more aspects, the method includes comparing the determined change in the tubing OD to an established occlusion dimension change threshold, generating a signal based on the determined change in tubing OD exceeding the established occlusion dimension change threshold and transmitting the signal to the fluid flow pump through a feedback loop. In one or more aspects, the method includes adjusting a pumping rate of the fluid flow pump based on receipt of the signal from the feedback loop to maintain a predetermined flow rate accuracy range. In one or more aspects, the method includes comparing the determined change in the tubing OD to an established occlusion dimension change threshold and generating an alarm by an interface when the established occlusion dimension change threshold is exceeded.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
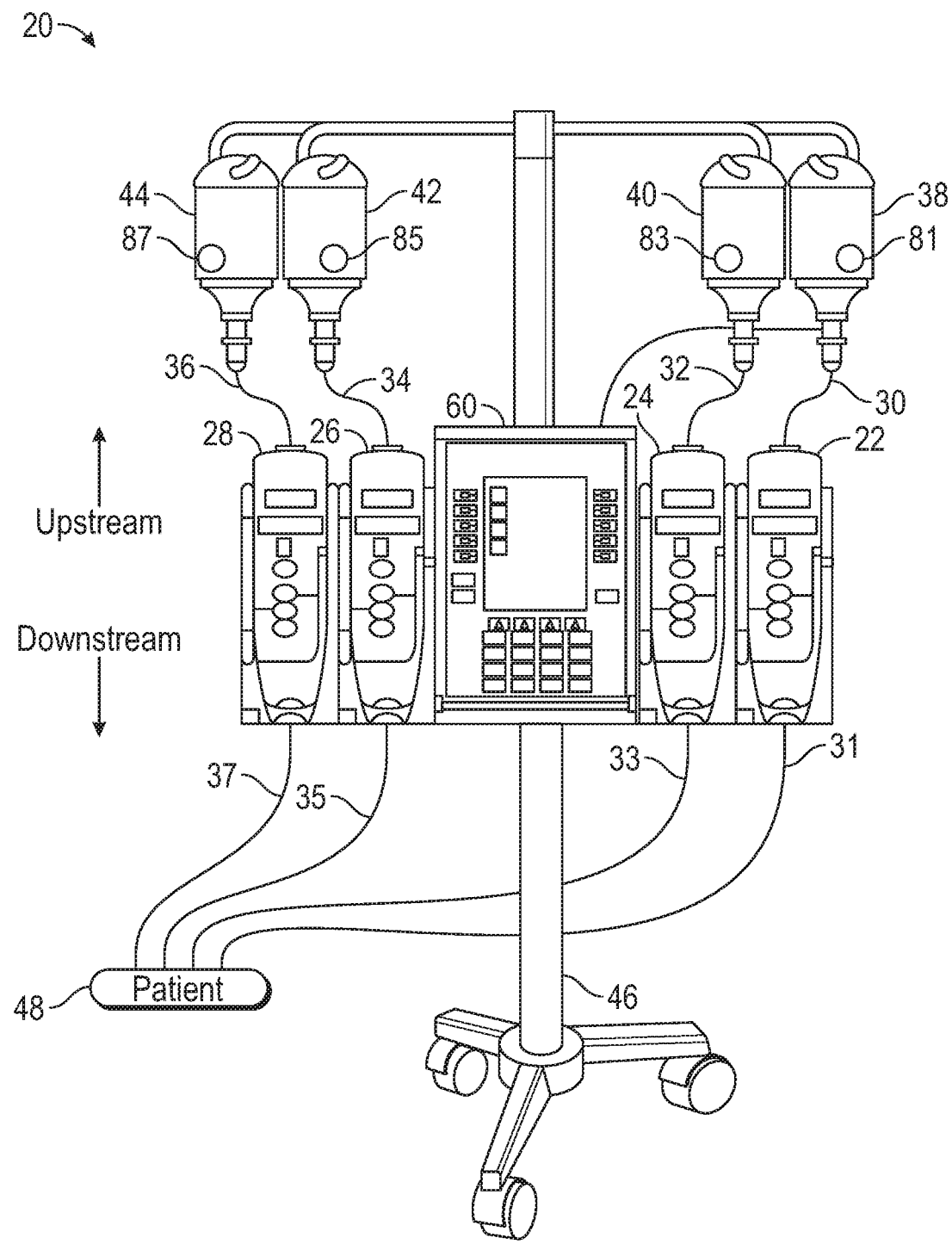
FIG. 1 depicts a front view of an example patient care system having four fluid infusion pumps, each of which is connected to a respective fluid supply for pumping the contents of the fluid supply to a patient, according to some aspects of the disclosure.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, table top, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or other fluids.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Typically, medical fluid administration sets have more parts than are shown in FIG. 1. Many have check valves, drip chambers, valves with injection ports, connectors, and other devices well known to those skilled in the art, such as output device 60. Some of these other devices have not been included in the drawings so as to preserve clarity of illustration.

Figure 2:
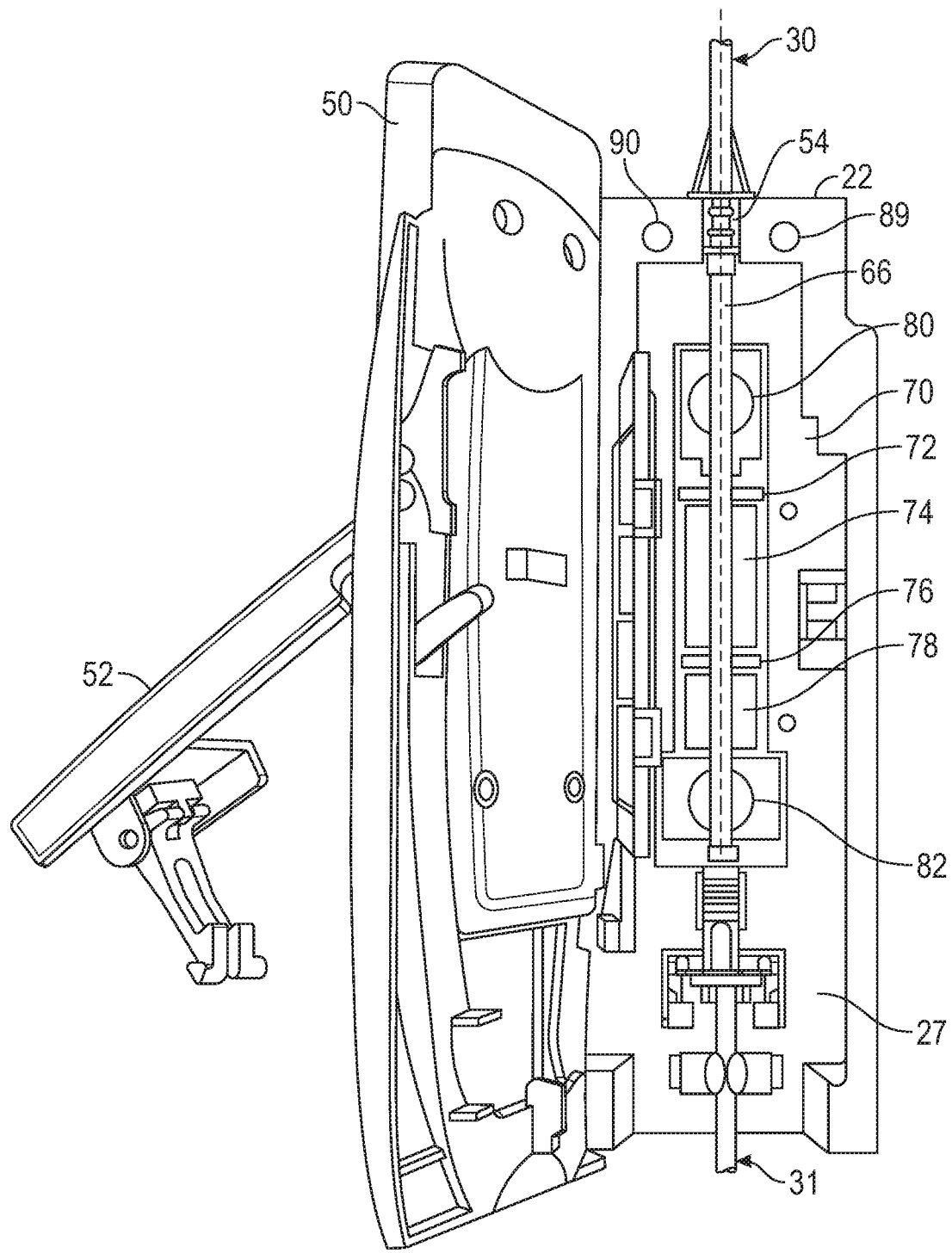
FIG. 2 depicts a perspective view of one of the fluid infusion pumps of FIG. 1, according to some aspects of the disclosure.

Turning now to FIG. 2, an infusion pump 22 having a body 27 is shown in perspective view with the front door 50 open, showing the upstream fluid line 30 and downstream fluid line 31 in operative engagement with the pump 22. The infusion pump 22 directly acts on a tube 66 that connects the upstream fluid line 30 to the downstream fluid line 31 to form a continuous fluid conduit, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 22.

The type of pumping mechanism may vary and may be for example, a multiple finger pumping mechanism. For example, the pumping mechanism may be of the "four finger" type and includes an upstream occluding finger 72, a primary pumping finger 74, a downstream occluding finger 76, and a secondary pumping finger 78. The "four finger" pumping mechanism and mechanisms used in other linear peristaltic pumps operate by sequentially pressing on a segment of the fluid conduit by means of the cam-following pumping fingers and valve fingers 72, 74, 76, and 78. The pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art and no further operational details are provided here.

FIG. 2 further shows a downstream pressure sensor 82 included in the pump 22 at a downstream location with respect to the pumping mechanism. The downstream pressure sensor 82 is mounted to the flow control device 70 and is located adjacent and downstream in relation to the flow control device. The downstream pressure sensor is located downstream from the flow control device, that is, at a location between the patient 48 (FIG. 1) and the flow control device, so that the connection of the correct fluid supply with the correct pump may be verified before any fluid is pumped to the patient.

With reference still to FIG. 2, an upstream pressure sensor 80 may also be included in the pump 22. The upstream pressure sensor is assigned to the flow control device or pumping mechanism 70 and, in this embodiment, is further provided as an integral part of the pump 22. It is mounted to the flow control device 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient.

The pump 22 or a portion of the pump 22 may also be equipped with an electronic data tag or data transmitter. For example, as shown in FIG. 2, pump 22 may be equipped with a data tag 89 or a reader device 90 for providing or receiving infusion data. The data reader devices may include RFID readers (or receivers) or other wireless devices that are compatible with the data tags associated with the fluid containers. A data transmitter may transmit interrogation signals to the electronic data tags 81, 83, 85, 87 associated with the fluid containers for obtaining infusion data from those tags. Although referred to as data transmitting devices or RFID tags or RFID transponders, data transmitting devices may also receive or read data and may also be writable.

Typically, medical tubing is a disposable product that is used once and then discarded. The medical tubing may be formed from any suitable material, (e.g., soft PVC, silicone, TPV (EPDM+PP), TPU, TPS (SBS/SEBS/SIS/SEPS) and its blending with polyolefin, TPEE (polyether ester) rubber). As shown in FIG. 2, medical tubing 66 may be inserted into or otherwise engaged by pump 22. Pump 22 may include any of Large Volume, patient-controlled analgesia (PCA), ambulatory pump or insulin pump that drive tubing segment (s) to deliver medication or nutrients into a patient's body in controlled amounts. The medical tubing 66 is compressed when the pump door 50 is closed. With the pump door 50 closed, the medical tubing 66 is constrained within a gap 54 and directly contacted by the upstream force sensor 80. As discussed above, there are many sources of variation in measuring the force on the medical tubing 66 by the sensor 80.

Figure 3:
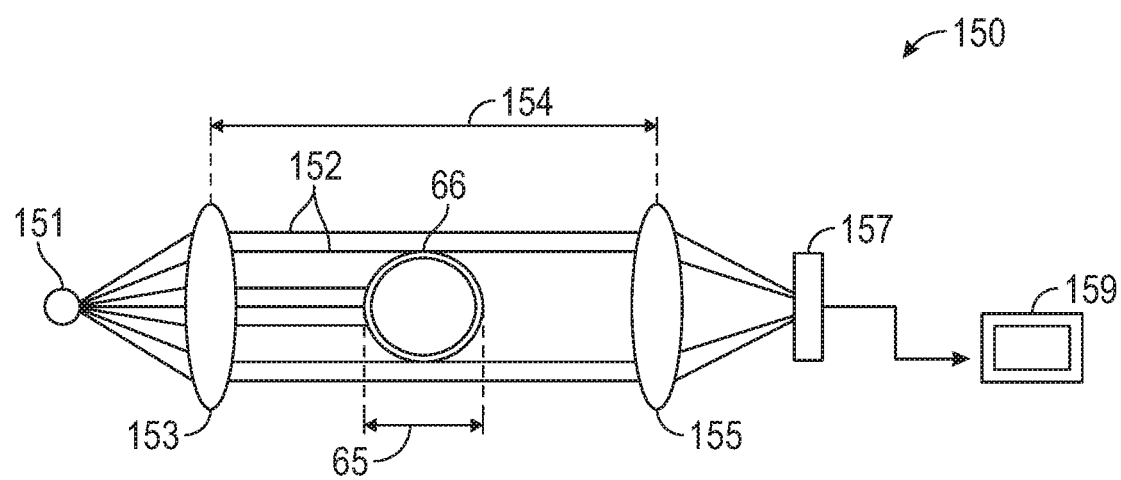
FIG. 3 depicts a schematic view of a non-contact tubing dimension measurement system, according to some aspects of the disclosure.

The present disclosure provides non-contact scanning (e.g., laser, optical, ultrasonic) to monitor tubing OD percentage change directly and in real time with an established occlusion dimension change threshold. To overcome the force measuring variances, a non-contact tubing dimension measurement system 150 may be used to replace a force sensor 80 as shown in FIG. 3. Measurement system 150 may be an optical based system, a laser (e.g., scanning laser micrometer) including a source 151 (e.g., light emitting diode (LED), laser diode, helium-neon laser tube), a collecting lens 153 (e.g., collimator lens), a focal lens 155, an optical receiver 157 and a data processor 159. Here, light rays or beams 152 are reflected or refracted through a measurement area 154 in which a section of the medical tubing 66 is disposed. The section of the medical tubing 66 may be the segment disposed within the pump 22 or it may be a separate tubing segment in the fluid path. As shown in FIG. 3, some of the light beams 152 are blocked by the medical tubing 66, while the remaining unobstructed light beams 152 are focused by the focal lens 155 onto the optical receiver 157. The receiver 157 converts the received light beams 152 into data signals that are analyzed by the data processor 159 to determine the dimensions of the shadow caused by the medical tubing 66, which corresponds to the OD 65 of the medical tubing 66.

The non-contact tubing dimension measurement system 50 may monitor the medical tubing OD 65 percentage change directly and in real time during operation of the pump 22. The medical tubing OD 65 is monitored with an established occlusion dimension change threshold (e.g., 20% reduction of the initial tubing OD where the occlusion is defined to happen). If this threshold is exceeded, then an alarm may be triggered by a software and/or hardware interface. By using the non-contact tubing dimension measurement system 150, false alarms due to a soft medical tubing or larger gap between the back-support and gauge that are common with a typical force gauge setup are eliminated.

During pump 22 operation, the medical tubing 66 may collapse in random and non-predictable directions. To overcome this issue, the source 151 may require more than one from different angles to use to increase the measurement accuracy. The laser source may be a dual-axis, triple axis or quartic-axis scanning laser micrometer instead of a single-axis scanning laser micrometer. Further, the non-contact tubing dimension measurement system 150 may use other non-contact technologies for measuring and/or monitoring medical tubing 66. For example, the source 151 may be an ultrasonic transducer that emits high-frequency sound waves that bounce off of the medical tubing 66 and echo back to the transducer. Here, each received echo is converted into electrical energy that is then analyzed by the data processor 159, which may be a digital signal processor (DSP).

In some aspects, a feedback loop mechanism is provided to communicate between the tubing deformation dynamics and pumping rate during delivery to gain improved flow delivery accuracy. Some dedicated infusion sets may use non-silicone pumping tubing material for cost-saving purposes. However, silicone-alike materials, such as plasticized high molecular weight PVC or Styrenic Blocking Copolymer TPE typically do not compare favorably with silicone material due to silicone's superior elasticity and less sensitivity to temperature change. Thus, a delivery accuracy challenge for non-silicone tubing material is that the tubing does not bounce back quickly enough to the full volume per stroke under lower temperature at high flow rate. In particular, the non-silicone tubing material generally becomes stiffer and loses some elasticity performance at low temperature in the application temperature window from 5° C. to 40° C. In such cases, the non-silicone tubing material does not recover fully and quickly to its desired round shape prior to the next pumping cycle.

Based on the non-silicone tubing material issues discussed above, a typical pumping process leads to pumping cycles resulting in a lower delivery volume. Accordingly, the pump will fail the flow rate target if the pump is unable to feed back the volume insufficiency information to increase the pumping speed to compensate the partially refilled volume.

Some aspects of the disclosure provide using the non-contact tubing dimension measurement system 150 to sense a tubing refilled position of each pumping cycle. For example, the non-contact tubing dimension measurement system 150 may measure the tubing OD 65 change during the pumping cycle with an established OD vs. volume transfer function equation. A signal may by generated based on the measured tubing OD 65 change and the signal may be fed back (e.g., feedback loop) to a pump system 25 (e.g., patient care system 20, pump 22). Based upon the feedback signal, the pump system 25 may adjust the frequency of pumping cycles to maintain an acceptable (e.g., predetermined) flow rate accuracy range.

For example, when the pump 22 executes a pump cycle by compressing the tubing 66, the non-contact tubing dimension measurement system 150 measures the tubing OD 65 change as the tubing 66 attempts to spring back to an optimal full round shape once the compressive force exerted by the pump 22 ceases. Here, the non-contact tubing dimension measurement system 150 measures the actual tubing OD 65 after compression and a feedback signal is generated based on a predetermined measured OD vs. volume equation or table. The pump system 25 receives the feedback signal and adjusts the frequency of pumping rate cycles 66. For example, if the measured OD 65 is ten percent below the optimal fully round OD 65, then the pump system 25 may increase the frequency of pumping cycles 66 where the higher pumping frequency causes the fluid to flow through the tubing 66 at a rate that is closer to the programmed rate. Thus, the non-contact tubing dimension measurement system 150 provides continuous, real time feedback signals to the pump system 25 to allow adjustments that minimize or eliminate undesired variations in fluid flow throughout the pumping system process.

Figure 4:
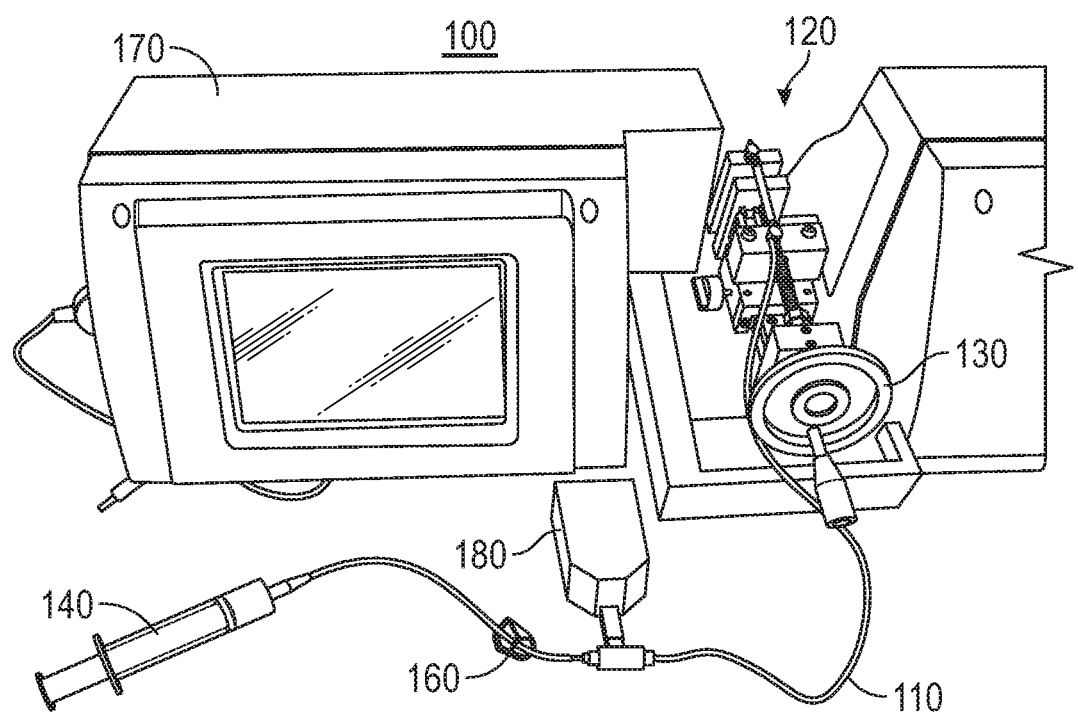
FIG. 4 depicts a perspective view of a test loop using a non-contact tubing dimension measurement system, according to some aspects of the disclosure.

In an example test, a benchtop model 100 was provided to simulate the relationship between OD change and vacuum pressure in order to mimic tubing OD change under occlusion. As shown in FIG. 4, a 3" long tubing 110, (e.g., DEHA plasticized PVC tubing with hardness Shore A 70, non-sterile) was cut and inserted into a testing loop 120. The testing loop 120 includes a customized connection fixture 130 shown in FIG. 5. The testing loop 120 also includes a 10 mL syringe 140 to control the vacuum through the pre-filled water and a vacuum gauge 180 to measure the pressure. The testing loop 120 further includes pinch clamps 160 that control the fluid path. A one-axis scanning laser 170 is used to measure the tubing 110 OD change under different pressure (psi) to have a stable OD reading when the desired vacuum pressure is reached by manually moving the syringe 140 plunger and the pinch clamp 160 is closed. In the example, measurements were made three times using the same tubing 110.

Figures 5, 6:
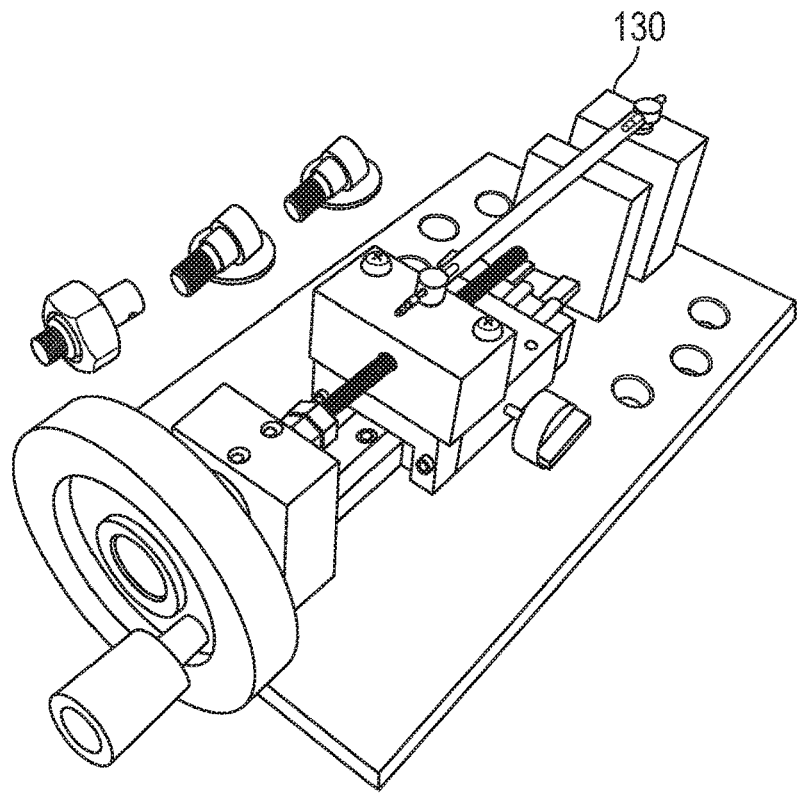
FIG. 5 depicts a perspective view of a connection fixture used in the test loop of FIG. 4, according to some aspects of the disclosure.
FIG. 6 is a table of test results related to tubing OD change vs. variable vacuum pressure, according to some aspects of the disclosure.

The test data from the example is summarized in Table 1, shown in FIG. 6. Here, for each of Test 1, Test 2 and Test 3, the OD of tubing 110 was measured by the one-axis scanning laser 170 after different vacuum pressures were applied. As seen in Table 1, the smaller the OD (e.g., the greater the tube deformation) the greater the vacuum pressure required. As also shown, the total OD change through the five negative pressure cycles is significant, ranging from 17.7% to 21.1% change in OD. Table 1 data is also shown as a corresponding graphical plot in FIG. 7.

Figure 7:
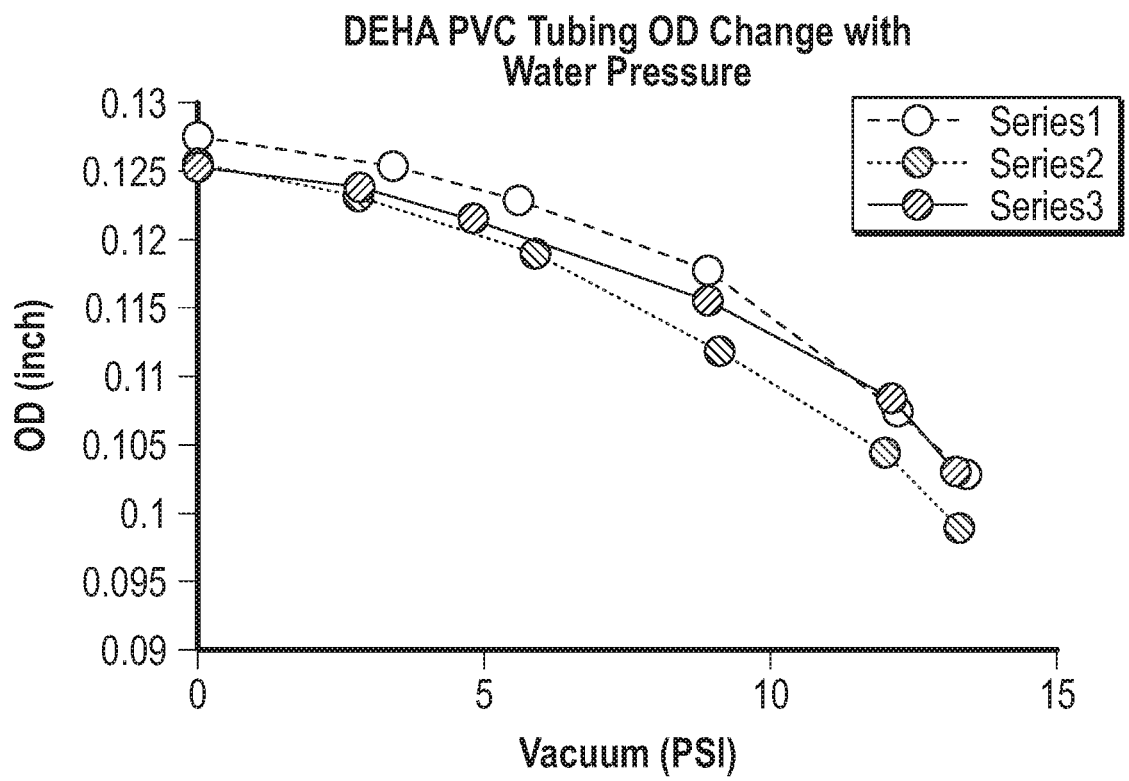
FIG. 7 is a graphical representation of the test results of FIG. 6, according to some aspects of the disclosure.

As shown in FIGS. 6 and 7, the percentage change of OD from initial to the end was approximately 20% under approximately 13 psi vacuum. Thus, as an example, an OD percentage change of 20% in the diameter of the tubing measured by the non-contact tubing measurement system 150 could be defined as a threshold to trigger an occlusion alarm. Further, the tubing 66 may be formed from a soft elastomeric material (e.g., soft PVC, silicone, TPV (EPDM+PP), TPU, TPS (SBS/SEBS/SIS/SEPS) and its blending with polyolefin, TPEE (polyether ester) rubber) with hardness shore A in the range of 40 to 90. The hardness shore A may also be provided in a tighter range of 50 to 80 or in an even tighter range of 60 to 70.

Figure 8A:
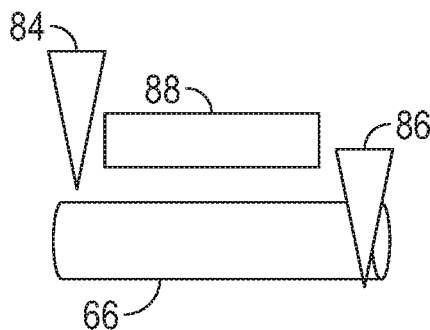
FIGS. 8A-8C depict a schematic view of a pump cycle, according to some aspects of the disclosure.
Figure 8B:
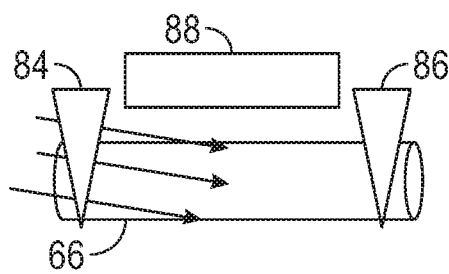
Figure 8C:
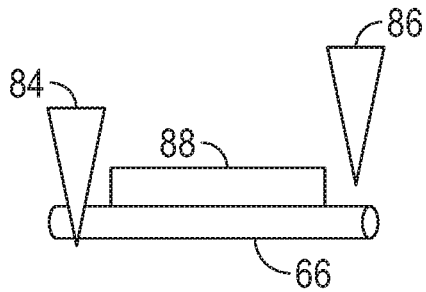

In FIGS. 8A-8C, an exemplary pump cycle is shown. In FIG. 8A, an upstream occlusion valve 84 is open, a downstream occlusion valve 86 is closed and a plunger 88 is lifted up, thus allowing for the tubing 66 to fill with fluid without passing directly through to the patient. As shown in FIG. 8B, the upstream occlusion valve 84 then closes while the plunger 88 remains lifted up and an OD measurement of tubing 66 is detected (e.g., by non-contact tubing measurement system 150). The detected OD measurement may be fed back to a pump system (e.g., pump system 25). In FIG.

8C, the downstream occlusion valve 86 is opened while the upstream occlusion valve remains closed and the plunger 88 pushes down on the tubing 66, thus allowing the fluid to flow downstream to the patient.

Figure 9A:
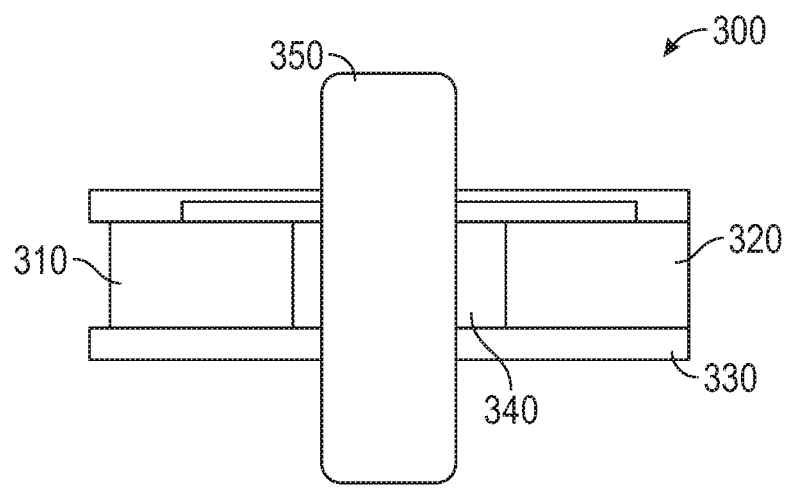
FIGS. 9A and 9B depict front and top views of a detector assembly, according to some aspects of the disclosure.
Figure 9B:
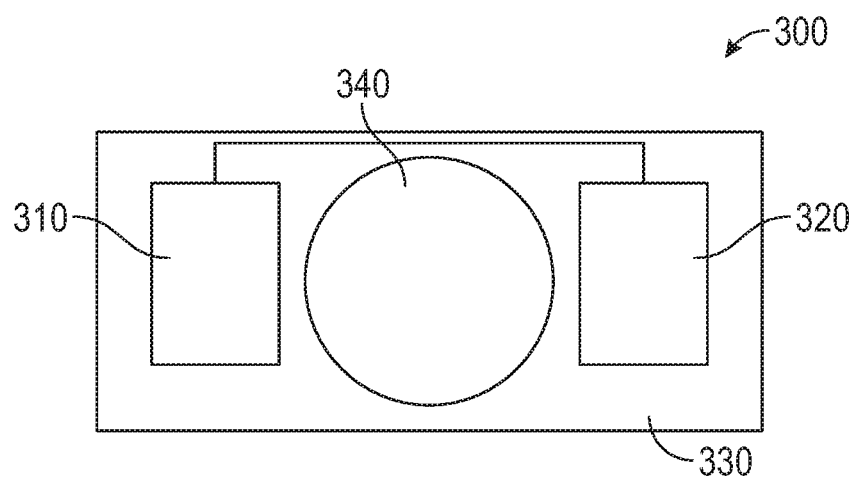

FIGS. 9A and 9B show an example of a detector assembly 300 that may be separate from a pump (e.g., pump 22). The detector assembly 300 may include an emitter 310 and a collector 320 disposed in a housing 330. The housing 330 may have a central opening or hole 340 through which tubing 350 (e.g., upstream fluid line 30, downstream fluid line 31) is disposed. The hole 340 may include rubber or any other anti-slip material to allow the detector assembly 300 to be affixed to a location on the tubing 350. The housing 330 may include any of source, sensor and communications components. The communications may include an alert function (e.g., audio, visual) and/or full data communications with an external controller or processor. Thus, the detector assembly 300 may include any or all of the components of non-contact tubing measurement system 150.

The detector assembly 300 may be integrated wholly or partially with a pump (e.g., pump 22). For example, the detector assembly 300 may be disposed within or on the pump door 50, the detector assembly 300 may be disposed within or on the body 27 of the pump 22, and a portion of the detector assembly 300 may be disposed within or on the pump door 50 and another portion of the detector assembly 300 may be disposed within or on the pump body 27.

Figure 10:
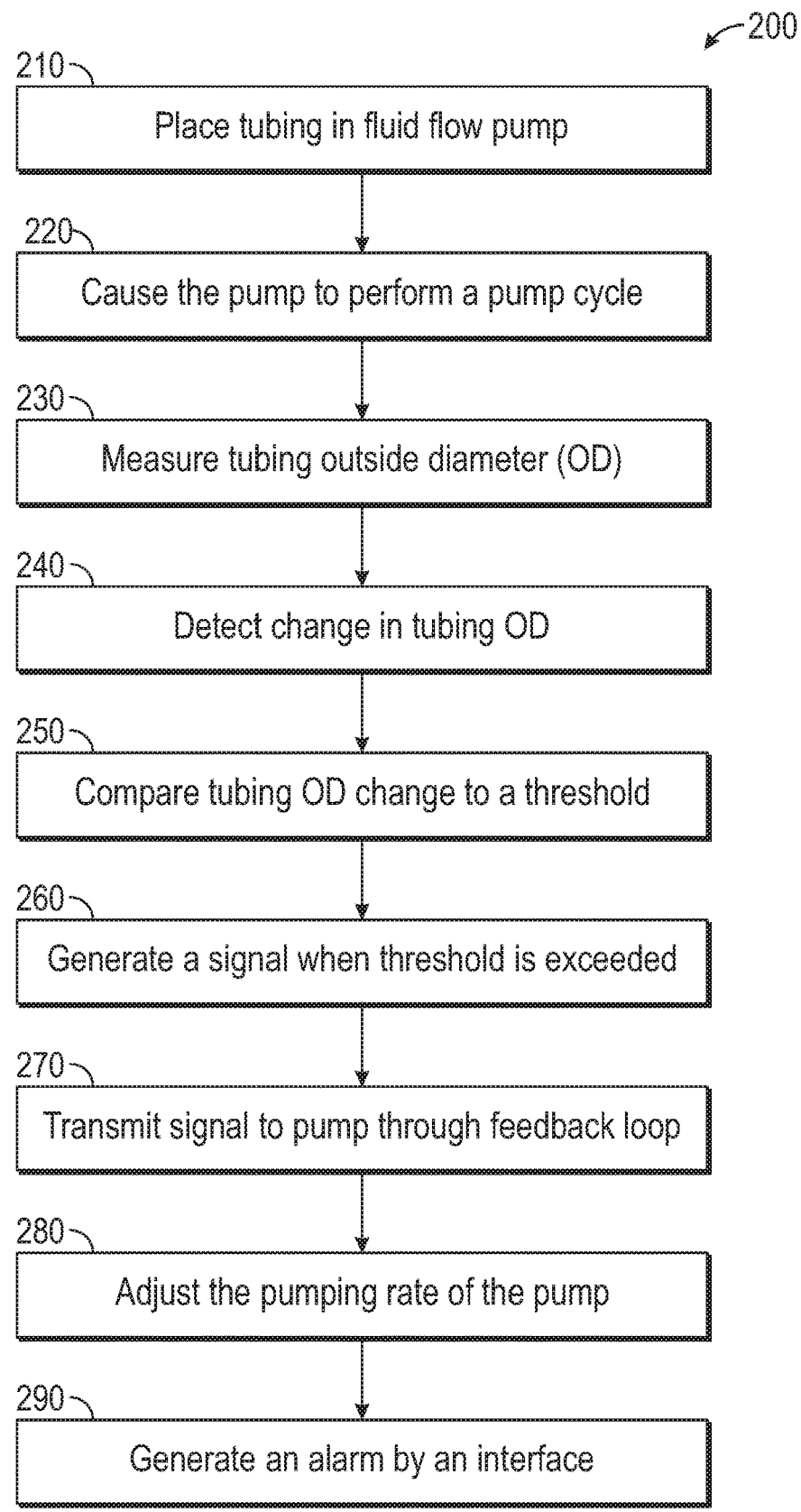
FIG. 10 depicts a flow diagram of a method of using a non-contact tubing dimension measurement system, according to some aspects of the disclosure.

FIG. 10 shows a method of operating a fluid flow pump 200. In step 210, tubing (e.g., IV tubing) is placed or disposed in a fluid flow pathway of a fluid flow pump. For example, tubing may be inserted into a fluid flow pathway of an open fluid flow pump and a door of the pump may then be closed to secure the tubing within the fluid flow pathway of the pump. The pump is cycled in step 220. For example, the pump may cause a compression force to squeeze any or all of the tubing in the fluid flow pathway, causing the fluid in the tubing to flow out of the tubing exiting the pump. The compression force may be a recurring force where each compression is a pump cycle. In step 230, the recovered tubing OD is measured after the fluid is refilled during each pump cycle, where the measurement is by a non-contact tubing dimension measurement assembly or device. Thus, the measurement assembly does not physically engage the tubing.

In step 240, a change in the tubing OD is detected based on a previous cycle's tubing OD measurement after the fluid filling. The OD measurement is made before the compression of the tubing and after the completion of a compression pump cycle. For example, the optimum result would be zero change in the tubing OD before and after the compression pump cycle, which would indicate that the tubing was resilient enough for the tubing to pop back out to its initial round shape. However, the more likely outcome is for the tubing to regain most, but not all, of its initial round shape after the compression force is removed from the tubing, resulting in a change in the tubing OD. The change in tubing OD may be detected in real-time during continuous operation of the pump.

The detected change in tubing OD is compared to an established occlusion dimension change threshold (e.g., predetermined threshold value) in step 250. In step 260, a signal is generated if the detected change in tubing OD exceeds the established occlusion dimension change threshold. For example, the signal may be a fault signal due to occlusion of the tubing. The signal is transmitted to the fluid flow pump through a feedback loop in step 270. In step 280, the fluid flow pump adjusts the pumping rate (to maintain the programmed flow rate. For example, if the tubing OD only bounces back to 80% of its original tubing OD after a compression cycle, the next compression cycle will result in "$0.80^2 * 100$"% of the target delivered volume. In order to compensate for this rate error/variation, the pump may increase the frequency of subsequent pumping cycles. In step 290, an alarm may be generated by an interface when the established occlusion dimension change threshold is exceeded. For example, the signal generated in step 260 may be received by the interface, thus causing the interface to generate (e.g., trigger) the alarm.

According to some aspects of the disclosure, a pump assembly includes a fluid flow pump, a tubing pathway configured to receive a fluid tube and a tubing dimension measurement assembly. The tubing dimension measurement assembly includes a processor, an emitter spaced from the tubing pathway and configured to generate an emission into the tubing pathway, and a collector spaced from the tubing pathway, the collector disposed to receive the emission from the emitter, wherein the tubing dimension measurement assembly is further configured to measure an outside diameter (OD) of a tube received in the pathway, wherein said measurement is based at least in part on the emission.

According to some aspects of the disclosure, the fluid flow pump is an infusion pump. According to some aspects of the disclosure, the tubing dimension measurement assembly is disposed on a portion of the tubing pathway receiving a fluid input tube. According to some aspects of the disclosure, the tubing dimension measurement assembly is disposed either internal or external to the fluid flow pump. According to some aspects of the disclosure, the tubing dimension measurement assembly comprises a laser scanning system including the emitter and the collector. According to some aspects of the disclosure, the laser scanning system includes one of a single-axis, dual-axis, a triple-axis and a quartic-axis scanning laser micrometer. According to some aspects of the disclosure, the tubing dimension measurement assembly comprises an ultrasonic scanning system including the emitter and the collector. According to some aspects of the disclosure, the tubing dimension measurement assembly is further configured to monitor a change in measurements of the OD in real time during operation of the fluid flow pump.

According to some aspects of the disclosure, the processor is configured to detect a change in the OD exceeding an occlusion dimension change threshold. According to some aspects of the disclosure, the processor is further configured to cause presentation of an alarm upon detecting that the established occlusion dimension change threshold is exceeded. According to some aspects of the disclosure, the tubing dimension measurement assembly is configured to detect a tubing refilled position of each pumping cycle. According to some aspects of the disclosure, the processor is configured to measure a change in the tubing OD with a predetermined measured OD vs. volume equation or table. According to some aspects of the disclosure, the processor is configured to generate a signal based on the measured change in OD, wherein the signal causes an adjustment to at least one operational characteristic of the pump assembly. According to some aspects of the disclosure, the pump assembly includes an output device, and wherein the adjustment includes activating the output device based on the signal to provide a perceivable indication of the change in OD. According to some aspects of the disclosure, the fluid flow pump is configured to adjust a pumping rate based on receipt of the signal to maintain a predetermined flow rate accuracy range.

According to some aspects of the disclosure, a method of operating a fluid flow pump includes disposing tubing in a fluid flow pathway of a fluid flow pump, causing the fluid flow pump to perform one or more pumping cycles, wherein each pumping cycle forces fluid flow from an output end of the tubing by exerting at least one force on a first portion of the tubing, and measuring, by a non-contact tubing dimension measurement assembly, a tubing outside diameter (OD) of the first portion of the tubing.

According to some aspects of the disclosure, the method includes determining a change in the tubing OD in real time during operation of the fluid flow pump. According to some aspects of the disclosure, the method includes comparing the determined change in the tubing OD to an established occlusion dimension change threshold, generating a signal based on the determined change in tubing OD exceeding the established occlusion dimension change threshold and transmitting the signal to the fluid flow pump through a feedback loop. According to some aspects of the disclosure, the method includes adjusting a pumping rate of the fluid flow pump based on receipt of the signal from the feedback loop to maintain a predetermined flow rate accuracy range. According to some aspects of the disclosure, the method includes comparing the determined change in the tubing OD to an established occlusion dimension change threshold and generating an alarm by an interface when the established occlusion dimension change threshold is exceeded.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A pump assembly, comprising:
   a fluid flow pump;
   a tubing pathway configured to receive a fluid tube; and
   a tubing dimension measurement assembly including:
      a processor;
      a housing comprising an opening configured to receive a tube, the opening comprising an anti-slip material configured to affix the tubing dimension measurement assembly to a location on the tube;
      an emitter disposed in the housing and spaced from the tubing pathway, the emitter configured to generate an emission into the tubing pathway; and
      a collector disposed in the housing and spaced from the tubing pathway, the collector disposed to receive the emission from the emitter, wherein the tubing dimension measurement assembly is further configured to measure an outside diameter (OD) of the tube received in the pathway without physical contact, wherein said measurement is based at least in part on the emission,
      wherein the tubing dimension measurement assembly is further configured to monitor a change in measurements of the OD without physical contact in real time during operation of the fluid flow pump.

2. The pump assembly of claim 1, wherein the fluid flow pump is an infusion pump.

3. The pump assembly of claim 1, wherein the tubing dimension measurement assembly is disposed on a portion of the tubing pathway receiving a fluid input tube.

4. The pump assembly of claim 1, wherein the tubing dimension measurement assembly comprises a triple-axis laser scanning system including the emitter and the collector.

5. The pump assembly of claim 1, wherein the tubing dimension measurement assembly comprises a quartic-axis scanning laser micrometer including the emitter and the collector.

6. The pump assembly of claim 1, wherein the tubing dimension measurement assembly comprises an ultrasonic scanning system including the emitter and the collector.

7. The pump assembly of claim 1, wherein the processor is configured to detect a change in the OD exceeding an occlusion dimension change threshold.

8. The pump assembly of claim 7, wherein the processor is further configured to cause presentation of an alarm upon detecting that the established occlusion dimension change threshold is exceeded.

9. The pump assembly of claim 1, wherein the tubing dimension measurement assembly is configured to detect a tubing refilled position of each pumping cycle.

10. The pump assembly of claim 1, wherein the processor is configured to measure a change in the tubing OD with a predetermined measured OD vs. volume equation or table.

11. The pump assembly of claim 10, wherein the processor is configured to generate a signal based on the measured change in OD, wherein the signal causes an adjustment to at least one operational characteristic of the pump assembly.

12. The pump assembly of claim 11, wherein the pump assembly includes an output device, and wherein the adjustment includes activating the output device based on the signal to provide a perceivable indication of the change in OD.

13. The pump assembly of claim 11, wherein the fluid flow pump is configured to adjust a pumping rate based on receipt of the signal to maintain a predetermined flow rate accuracy range.

14. A method of operating a fluid flow pump, comprising:
    disposing tubing in a fluid flow pathway of a fluid flow pump;
    disposing a non-contact tubing dimension measurement assembly at a location on the tubing, the tubing being received through an opening having an anti-slip material affixing the non-contact tubing dimension measurement assembly at the location on the tubing;
    causing the fluid flow pump to perform one or more pumping cycles, wherein each pumping cycle forces fluid flow from an output end of the tubing by exerting at least one force on a first portion of the tubing;
    measuring, by the non-contact tubing dimension measurement assembly, a tubing outside diameter (OD) of the first portion of the tubing; and
    determining a change in the tubing OD in real time during operation of the fluid flow pump.

15. The method of claim 14, further comprising:
    comparing the determined change in the tubing OD to an established occlusion dimension change threshold;
    generating a signal based on the determined change in tubing OD exceeding the established occlusion dimension change threshold; and
    transmitting the signal to the fluid flow pump through a feedback loop.

16. The method of claim 15, further comprising:
    adjusting a pumping rate of the fluid flow pump based on receipt of the signal from the feedback loop to maintain a predetermined flow rate accuracy range.

17. The method of claim 14, further comprising:
    comparing the determined change in the tubing OD to an established occlusion dimension change threshold; and
    generating an alarm by an interface when the established occlusion dimension change threshold is exceeded.

18. The pump assembly of claim 1, wherein the anti-slip material is rubber.

19. The pump assembly of claim 1, wherein the tubing dimension measurement assembly is disposed external to the fluid flow pump.

* * * * *